US012618032B2

(12) United States Patent
Hamachi et al.

(10) Patent No.: US 12,618,032 B2
(45) Date of Patent: May 5, 2026

(54) METHOD FOR PRODUCING ORGANIC SUBSTANCE AND DEVICE FOR PRODUCING ORGANIC SUBSTANCE

(71) Applicant: SEKISUI CHEMICAL CO., LTD., Osaka (JP)

(72) Inventors: Kokoro Hamachi, Tokyo (JP); Satoshi Shimizu, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 910 days.

(21) Appl. No.: 17/794,447

(22) PCT Filed: Jan. 21, 2021

(86) PCT No.: PCT/JP2021/002027
§ 371 (c)(1),
(2) Date: Jul. 21, 2022

(87) PCT Pub. No.: WO2021/149764
PCT Pub. Date: Jul. 29, 2021

(65) Prior Publication Data
US 2023/0047619 A1     Feb. 16, 2023

(30) Foreign Application Priority Data
Jan. 23, 2020    (JP) ................................. 2020-009375

(51) Int. Cl.
| | |
|---|---|
| *C12P 7/08* | (2006.01) |
| *C10L 3/06* | (2006.01) |
| *C12M 1/00* | (2006.01) |
| *C12P 7/06* | (2006.01) |

(52) U.S. Cl.
CPC .............. *C12M 21/12* (2013.01); *C12P 7/08* (2013.01)

(58) Field of Classification Search
CPC .......... C10J 3/18; C12M 43/04; C12M 29/26; C12M 4/34; C12M 21/02; C12P 7/08; C12P 7/06
See application file for complete search history.

(56) References Cited

U.S. PATENT DOCUMENTS

| | | | |
|---|---|---|---|
| 5,866,091 | A | 2/1999 | Stevenson et al. |
| 6,463,864 | B2 | 10/2002 | Yamamoto et al. |
| 9,410,095 | B2 | 8/2016 | Zhang et al. |
| 10,577,577 | B2 | 3/2020 | Satou et al. |
| 10,865,425 | B2 | 12/2020 | Fujimori et al. |
| 2002/0033123 | A1 | 3/2002 | Yamamoto et al. |
| 2008/0299650 | A1 | 12/2008 | Krieg |
| 2009/0038316 | A1 | 2/2009 | Pearson |
| 2010/0051875 | A1* | 3/2010 | Chornet ................... C10K 3/04 252/373 |
| 2010/0298450 | A1 | 11/2010 | Datta et al. |
| 2012/0052541 | A1 | 3/2012 | Oakley |
| 2012/0142522 | A1 | 6/2012 | Pearson |
| 2012/0291351 | A1 | 11/2012 | Bool et al. |
| 2013/0137151 | A1 | 5/2013 | Tobey et al. |
| 2013/0149755 | A1 | 6/2013 | Reed et al. |
| 2014/0131622 | A1 | 5/2014 | Winter et al. |
| 2014/0272734 | A1 | 9/2014 | Braun et al. |
| 2014/0305043 | A1 | 10/2014 | Zhang et al. |
| 2016/0222340 | A1 | 8/2016 | Satou et al. |
| 2019/0256874 | A1 | 8/2019 | Fujimori et al. |
| 2020/0048665 | A1 | 2/2020 | Simpson |
| 2021/0054418 | A1 | 2/2021 | Nishiyama et al. |
| 2021/0054419 | A1 | 2/2021 | Fujimori et al. |

FOREIGN PATENT DOCUMENTS

| | | | |
|---|---|---|---|
| CA | 2861819 | * | 7/2013 |
| CN | 102803497 | | 11/2012 |
| CN | 108722173 | | 11/2018 |
| JP | 2001-314725 | | 11/2001 |
| JP | 2003-225642 | | 8/2003 |
| JP | 3558039 | | 8/2004 |
| JP | 2004-249203 | | 9/2004 |
| JP | 2006-104339 | | 4/2006 |
| JP | 2007-45857 | | 2/2007 |
| JP | 2007-237135 | | 9/2007 |
| JP | 2009-298825 | | 12/2009 |
| JP | 2012-1441 | | 1/2012 |
| JP | 2012-149089 | | 8/2012 |
| JP | 2014-125577 | | 7/2014 |
| JP | 2014-227450 | | 12/2014 |
| JP | 2015-510522 | | 4/2015 |

(Continued)

OTHER PUBLICATIONS

International Search Report (ISR) issued Mar. 2, 2021 in International (PCT) Application No. PCT/JP2021/002027.
International Search Report (ISR) issued Mar. 2, 2021 in International (PCT) Application No. PCT /JP2021/002028.
Office Action issued Dec. 16, 2024 in related U.S. Appl. No. 17/794,388.
Nie, H.H., "Production of Sulphite Pulp," Chemical Pulp Technology, vol. 1, Light Industry Press, pp. 221-228, May 1960 (with partial English translation (3 pages)).
Notice of Allowance issued Apr. 10, 2025, in related U.S. Appl. No. 17/794,388.

(Continued)

*Primary Examiner* — Maryam Monshipouri
(74) *Attorney, Agent, or Firm* — Wenderoth, Lind & Ponack, L.L.P.

(57) ABSTRACT

A method for producing an organic substance includes a step of passing a synthesis gas G1 discharged from a gasifier 11 through a gas cooling tower 21 to cool the synthesis gas G1 with water sprayed in the gas cooling tower 21, a step of passing the synthesis gas G1 cooled in the gas cooling tower 21 through a filtration-type dust collector 22 and a step of bringing a synthesis gas G2 that has passed through at least the gas cooling tower 21 and the filtration-type dust collector 22 into contact with a microbial catalyst to generate an organic substance.

9 Claims, 1 Drawing Sheet

(56) References Cited

FOREIGN PATENT DOCUMENTS

| JP | 2017-216997 | 12/2017 |
|----|-------------|---------|
| JP | 2018-58042 | 4/2018 |
| JP | 2019-88240 | 6/2019 |
| JP | 2019-167424 | 10/2019 |
| WO | 2009/157788 | 12/2009 |
| WO | 2010/126382 | 11/2010 |
| WO | 2011/087380 | 7/2011 |
| WO | 2015/037710 | 3/2015 |
| WO | 2019/188730 | 10/2019 |

OTHER PUBLICATIONS

Do et al. "Growth of Rhodospirillum rubrum on Synthesis Gas: Conversion of CO to H2 and Poly-B-hydroxyalkanoate." Biotechnology and Bioengineering, vol. 97, No. 2 (Jun. 1, 2007), pp. 279-286. (Year: 2007).

Wang et al. "Dust and Toxic Gas Control Technology", Inner Mongolia University Press, p. 181 (2012).

International Preliminary Report on Patentability issued Mar. 15, 2016 in International Application No. PCT/JP2014/074258.

Extended European Search Report issued Apr. 7, 2017 in corresponding European Application No. 14843678.5.

Office Action issued Sep. 10, 2018 in Chinese Application No. 201480049178.3, with English-language translation of Search Report.

Bartocci, "Wet Scrubbers for Gasifier Gas Cleaning", Paper #49 (1998), http://www.elmiraohio.com/GasifierDocs/Wet_Scrubbers.pdf.

Tashikazu Ooya et al., Chapter V. Demonstration Plan for Reforming Biogas and Introducing Energy Equipment, Report for Betsukai-cho Biomass Utilization Plan, pp. 99-114 (2006), with Partial Translation.

Munasinghe P.C. and Khanal S. K., "Syngas Fermentation to Biofuel: Evaluation of Carbon Monoxide Mass Transfer Coefficient (kLa) in Different Reactor Configurations", Biotechnology Progress, 26(6): 1616-1621 (2010).

Meier, "Using Venturi Scrubber Technology for Syngas Cleaning", APC (2013), 3 pgs. https://www.bionomicind.com/pdf/apc_Using VenturiScrubberTechnology for Syngas.pdf.

Written Opinion mailed Dec. 16, 2014 in International Application No. PCT/JP2014/074258.

International Search Report issued Dec. 16, 2014 in International (PCT) Application No. PCT/JP2014/074258.

Yukimoto et al., "Haikibutsu-kei Biomass no Yuko Riyo to sono Genjo in Kansuru Gijutsu Chosa Hokoku", Panel Discussion & Tokubetsu, Koen Haikibutsu-kei Biomass no Yuko Riyo no Genjo -Mokushitsu-kei Biomass-, Nov. 21, 2008, pp. 1-1 to 1-31, pp. 1-6, 1-11, fig. 3-2, partial English translation.

Zhang Xuzhi et al., "Petrochemical Engineering Series Ethylene Derivatives Engineering," Chemical Industry Press, Jul. 1995, pp. 1-6, with English machine translation.

* cited by examiner

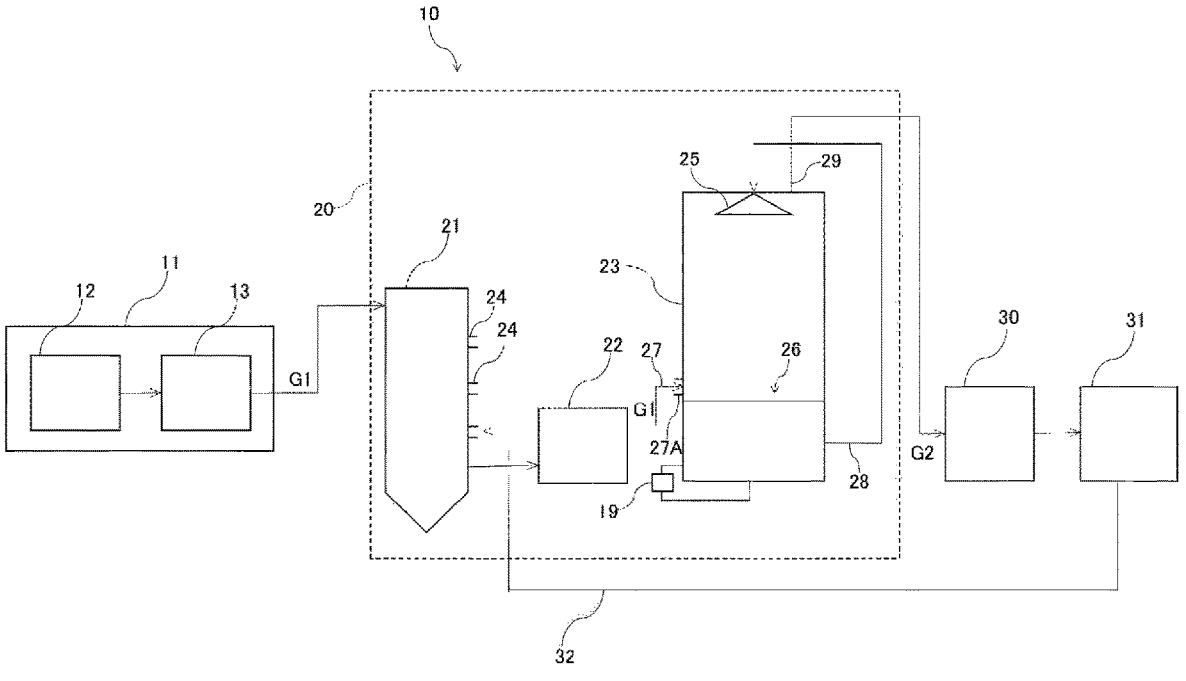

METHOD FOR PRODUCING ORGANIC SUBSTANCE AND DEVICE FOR PRODUCING ORGANIC SUBSTANCE

TECHNICAL FIELD

The present invention relates to a method for producing organic substance in which an organic substance is produced using a synthesis gas as a raw material and a device for producing an organic substance in which an organic substance is produced using a synthesis gas as a raw material.

BACKGROUND ART

Techniques that thermally decompose a variety of wastes such as industrial waste and general waste to generate a gas in a gasification furnace and then reform the generated gas to obtain a synthesis gas in a reforming furnace are broadly known. The obtained synthesis gas is combusted as it is and used for power generation or the like or is used for power generation or the like after heat is recovered with a boiler or the like as necessary.

In addition, recently, attempts have been underway to use a synthesis gas as a chemical synthesis raw material, and, for example, attempts have been underway to convert a synthesis gas to an organic substance such as ethanol using a microbial catalyst (for example, refer to PTLs 1 to 3).

Synthesis gases obtained in the gasification furnace and the reforming furnace contain a large amount of an impurity such as a tar component, and it is difficult to use the synthesis gases as they are for power generation and chemical synthesis, and thus it is ordinary to purify the gases. It is known that synthesis gas is cooled as appropriate during the purification of the gas. For example, PTL 4 discloses a method for purifying a gas in which a synthesis gas is guided to an indirect heat exchanger such as a boiler heat transfer pipe, cooled to approximately 300° C. to 600° C. by recovering heat, then, guided to a spray tower to remove approximately 50% of tar mist while the synthesis gas is cooled to a temperature of 100° C. or lower by water spray spraying and then guided to a wet-type electric dust collecting device to remove 90% or more of the remaining tar mist.

In addition, PTL 5 shows a method in which a harmful component such as tar or char is removed from an obtained synthesis gas with a bag filter. Ordinarily, it is not possible to pass high-temperature gas through a bag filter, and thus, in the present method, a gas cooler for cooling the synthesis gas is installed in the pre-stage of the bag filter, and the synthesis gas is cooled to approximately 200° C. before passing through the bag filter.

CITATION LIST

Patent Literature

PTL1: International Publication No. WO 2015/037710
PTL2; JP 2019-167424 A
PTL3: JP 2019-088240 A
PTL4: JP 2009-298825 A
PTL5: JP 2007-237135 A

SUMMARY OF INVENTION

Technical Problem

Incidentally, in a case where a synthesis gas is used as, for example, an organic synthesis raw material, it is necessary to strictly control the temperature in some cases. For example, in a case where a synthesis gas is converted to an organic substance such as ethanol using a microbial catalyst, it is necessary to cool the synthesis gas to a temperature of 40° C. or lower to prevent the death of the microbial catalyst.

However, in the case of using a synthesis gas for power generation or the like, strict temperature control is not required. In addition, it is ordinary that nitrogen or an air is often blown to cool a synthesis gas; however, in the case of using a microbial catalyst, nitrogen or an air mixed into the synthesis gas decreases the conversion efficiency of an organic substance. Therefore, even when the conventional methods for purifying a synthesis gas described in PTLs 4 and 5 are applied to the case of using a microbial catalyst as they are, it is difficult to synthesize organic substances at a high conversion efficiency.

Therefore, an objective of the present invention is to provide a method for producing an organic substance and a device for producing an organic substance that are capable of synthesizing an organic substance at a high conversion efficiency even in the case of converting a synthesis gas to an organic substance using, for example, a microbial catalyst.

Solution to Problem

As a result of intensive studies, the present inventors found that the above-described objective can be achieved by cooling a synthesis gas with water sprayed in a gas cooling tower and purifying the cooled synthesis gas using a filtration-type dust collector and completed the present invention below.

That is, the present invention provides [1] to [20] below.

[1] A method for producing an organic substance including a step of passing a synthesis gas discharged from a gasifier through a gas cooling tower to cool the synthesis gas with water sprayed in the gas cooling tower, a step of passing the synthesis gas cooled in the gas cooling tower through a filtration-type dust collector, and a step of bringing the synthesis gas that has passed through at least the gas cooling tower and the filtration-type dust collector into contact with a microbial catalyst to generate an organic substance.

[2] The method for producing an organic substance according to [1], in which a temperature of the synthesis gas discharged from the gasifier is 900° C. or higher.

[3] The method for producing an organic substance according to [1] or [2], in which the synthesis gas is cooled to a temperature of 100° C. or higher and 200° C. or lower in the gas cooling tower.

[4] The method for producing an organic substance according to any one of [1] to [3], in which the synthesis gas discharged from the filtration-type dust collector is further passed through a water scrubber, and the synthesis gas that has passed through at least the gas cooling tower, the filtration-type dust collector and the water scrubber is brought into contact with a microbial catalyst to generate an organic substance.

[5] The method for producing an organic substance according to [4], in which the synthesis gas is cooled to 40° C. or lower in the water scrubber.

[6] The method for producing an organic substance according to [4] or [5], in which the water sprayed in the gas cooling tower is vaporized and mixed into the synthesis gas, and at least a part of water mixed into the synthesis gas is condensed and removed in the water scrubber.

[7] The method for producing an organic substance according to any one of [1] to [6], in which the organic substance is generated in a reactor filled with at least the microbial catalyst and water, water is separated from an organic substance-containing liquid containing the organic substance obtained in the reactor, and the separated water is supplied to the gas cooling tower.

[8] The method for producing an organic substance according to any one of [1] to [7], in which the gasifier gasifies waste to generate a synthesis gas.

[9] The method for producing an organic substance according to any one of [1] to [8], in which the organic substance contains ethanol.

[10] A device for producing an organic substance including a gasifier that generates a synthesis gas, a gas cooling tower through which the synthesis gas discharged from the gasifier is passed to be cooled by water spray, a filtration-type dust collector through which the synthesis gas cooled in the gas cooling tower is passed, and an organic substance generation portion that brings the synthesis gas that has passed through at least the gas cooling tower and the filtration-type dust collector into contact with a microbial catalyst to generate an organic substance.

[11] The device for producing an organic substance according to [10], in which a temperature of the synthesis gas discharged from the gasifier is 900° C. or higher.

[12] The device for producing an organic substance according to [10] or [11], in which the synthesis gas is cooled to a temperature of 100° C. or higher and 200° C. or lower in the gas cooling tower.

[13] The device for producing an organic substance according to any one of [10] to [12], further including a water scrubber which is disposed in a post-stage of the filtration-type dust collector and through which the synthesis gas is passed, in which the organic substance generation portion brings the synthesis gas that has passed through at least the gas cooling tower, the filtration-type dust collector and the water scrubber into contact with the microbial catalyst to generate an organic substance.

[14] The device for producing an organic substance according to [13], in which the synthesis gas is cooled to 40° C. or lower with the water scrubber.

[15] The device for producing an organic substance according to [13] or [14], in which water sprayed in the gas cooling tower is vaporized and mixed into the synthesis gas, and at least a part of water mixed into the synthesis gas is condensed and removed in the water scrubber.

[16] The device for producing an organic substance according to any one of [10] to [15], in which the organic substance generation portion includes a reactor which is filled with at least the microbial catalyst and water and to which the synthesis gas is supplied,

the organic substance generation portion includes a separator that separates water from an organic substance-containing liquid containing the organic substance generated in the reactor, and the separated water is supplied to the gas cooling tower.

[17] The device for producing an organic substance according to any one of [10] to [16], in which the gasifier gasifies waste to generate a synthesis gas.

[18] The device for producing an organic substance according to any one of [10] to [17], in which the organic substance contains ethanol.

[19] A method for producing a purified synthesis gas including a step of gasifying waste to generate a synthesis gas in a gasifier, a step of passing the synthesis gas discharged from the gasifier through a gas cooling tower to cool the synthesis gas with water sprayed in the gas cooling tower, and a step of passing the synthesis gas cooled in the gas cooling tower through a filtration-type dust collector.

[20] A device for producing a purified synthesis gas including a gasifier that gasifies waste to generate a synthesis gas, a gas cooling tower through which the synthesis gas discharged from the gasifier is passed to be cooled by water spray, a filtration-type dust collector through which the synthesis gas cooled in the gas cooling tower is passed.

Advantageous Effects of Invention

According to the present invention, it becomes possible to synthesize an organic substance at a high conversion efficiency even in a case where synthesis gas is converted to an organic substance using, for example, a microbial catalyst.

BRIEF DESCRIPTION OF THE DRAWING

FIG. 1 is a schematic view showing the overall configuration of a device for producing an organic substance according to a first embodiment of the present invention.

DESCRIPTION OF EMBODIMENTS

Next, the present invention will be described using an embodiment with reference to a drawing.

FIG. 1 shows a device for producing an organic substance according to a first embodiment of the present invention. Hereinafter, a device for producing an organic substance and a method for producing an organic substance according to the embodiment of the present invention will be described in detail with reference to the first embodiment.

A device for producing an organic substance 10 includes a gasifier 11 that gasifies waste to generate synthesis gas G1, a treatment unit 20 that carried out a treatment including at least a purification treatment on the synthesis gas G1 discharged from the gasifier 11 and an organic substance generation portion 30 that generates an organic substance by bringing synthesis gas obtained by the treatment of the treatment unit 20 (hereinafter, also referred to as "purified synthesis gas G2") into contact with a microbial catalyst.

(Gasifier)

The waste that is gasified by the gasifier 11 may be industrial waste such as industrial solid waste or may be general waste such as municipal solid waste (MSW), and examples thereof include combustible substances such as plastic waste, raw garbage, discarded tires, biomass waste, food waste, building materials, wood, wooden chips, fibers and paper. Among these, municipal solid waste (MSW) is preferable.

The gasifier 11 includes a gasification furnace 12 and a reforming furnace 13. The gasification furnace 12 is not particularly limited, and examples thereof include a kiln gasification furnace, a fixed-bed gasification furnace, a fluidized-bed gasification furnace and the like. Into the gasification furnace 12, not only waste but also oxygen or an air and, furthermore, water vapor, if necessary, are injected. In the gasification furnace 12, the waste is heated at, for example, 500° C. to 700° C. and thereby thermally decomposed and partially oxidized as appropriate to be gasified. The thermally decomposed gas contains not only carbon monoxide and hydrogen but also gaseous tar, powdery char or the like. The thermally decomposed gas is supplied to the reforming furnace 13. A solid matter or the like that is generated as an impurity in the gasification furnace 12 is recovered as appropriate.

In the reforming furnace 13, the thermally decomposed gas obtained in the gasifier 11 is reformed, and the synthesis gas G1 is obtained. In the reforming furnace 13, the content rate of at least any of hydrogen and carbon monoxide in the thermally decomposed gas increases, and the thermally decomposed gas is discharged as the synthesis gas G1. In the reforming furnace 13, for example, tar, char or the like that is contained in the thermally decomposed gas is reformed into hydrogen, carbon monoxide or the like.

The temperature of the synthesis gas G1 in the reforming furnace 13 is not particularly limited, but is, for example, 900° C. or higher, preferably 900° C. or higher and 1300° C. or lower and more preferably 1000° C. or higher and 1200° C. or lower. When the temperature in the reforming furnace 13 is set within the above-described range, it becomes easy to obtain the synthesis gas G1 in which the content rates of carbon monoxide and hydrogen are high.

The temperature of the synthesis gas G1 that is discharged from the reforming furnace 13 (that is, gasifier 11) is the same as the temperature of the synthesis gas G1 and is, for example, 900° C. or higher, preferably 900° C. or higher and 1300° C. or lower and more preferably 1000° C. or higher and 1200° C. or lower.

The synthesis gas G1 that is discharged from the reforming furnace 13 (that is, gasifier 11) contains carbon monoxide and hydrogen. In addition, the synthesis gas G1 contains, for example, 0.1 vol % or more and 80 vol % or less of carbon monoxide and 0.1 vol % or more and 80 vol % or less of hydrogen.

The carbon monoxide concentration in the synthesis gas G1 is preferably 10 vol % or more and 70 vol % or less and more preferably 20 vol % or more and 55 vol % or less. In addition, the hydrogen concentration in the synthesis gas G1 is preferably 10 vol % or more and 70 vol % or less and more preferably 20 vol % or more and 55 vol % or less.

The synthesis gas G1 may contain, in addition to hydrogen and carbon monoxide, carbon dioxide, nitrogen, oxygen and the like. The carbon dioxide concentration in the synthesis gas G1 is not particularly limited, but is preferably 0.1 vol % or more and 40 vol % or less and more preferably 0.3 vol % or more and 30 vol % or less. In the case of generating ethanol using a microbial catalyst, it is particularly preferable to decrease the carbon dioxide concentration, and, from such a viewpoint, the carbon dioxide concentration is more preferably 0.5 vol % or more and 25 vol % or less.

The nitrogen concentration in the synthesis gas G1 is ordinarily 40 vol % or less and preferably 1 vol % or more and 20 vol % or less.

In addition, the oxygen concentration in the synthesis gas G1 is ordinarily 5 vol % or less and preferably 1 vol % or less. In addition, the oxygen concentration is preferably as low as possible as long as the oxygen concentration is 0 vol % or more. However, ordinarily, oxygen is inevitably contained in many cases, and the oxygen concentration is practically 0.01 vol % or more.

The concentrations of carbon monoxide, carbon dioxide, hydrogen, nitrogen and oxygen in the synthesis gas G1 can be set within predetermined ranges by appropriately changing combustion conditions such as the kind of the waste, the temperatures of the gasification furnace 12 and the reforming furnace 13 and the oxygen concentration of a supply gas that is supplied to the gasification furnace 11. For example, in a case where there is a desire to change the carbon monoxide or hydrogen concentration, the waste is changed to waste in which the rate of hydrocarbon (carbon and hydrogen) is high such as plastic waste, and, in a case where there is a desire to decrease the nitrogen concentration, a gas having a high oxygen concentration in the gasification furnace 12 is supplied.

Furthermore, in the synthesis gas G1, the concentration of each component such as carbon monoxide, carbon dioxide, hydrogen and nitrogen may be appropriately adjusted. The concentration is preferably adjusted by adding at least one of these components to the synthesis gas G1.

The volume percentage of each substance in the synthesis gas G1 described above means the volume percentage of each substance in the synthesis gas G1 that is discharged from the gasifier 11.

In the above description, an aspect in which the gasifier 11 includes the gasification furnace 12 and the reforming furnace 13 has been described, but the configuration of the gasifier 11 is not limited thereto, and the gasifier 11 may be a device in which a gasification furnace and a reforming furnace are integrated together and may be a gasifier of any type as long as the synthesis gas G1 can be generated.

(Gas Cooling Tower)

The treatment unit 20 in the present embodiment has at least a gas cooling tower 21, a filtration-type dust collector 22 and a water scrubber 23 as shown in FIG. 1. The synthesis gas G1 discharged from the gasifier 11 passes through the gas cooling tower 21. The gas cooling tower 21 is a facility that cools a gas that passes through the inside of the gas cooling tower 21 (synthesis gas G1) by water spray. The gas cooling tower 21 includes one or more water spray openings 24 for spraying water to the synthesis gas G1 on the inner peripheral surface. Two or more water spray openings 24 are preferably provided, and the two or more water spray openings 24 are more preferably provided at different height positions in the cooling tower 21. When a plurality of the water spray openings 24 is provided and, furthermore, the height positions thereof are different, it is possible to more sufficiently and efficiently cool the synthesis gas G1 by water spray.

In the gas cooling tower 21, it is preferable that the synthesis gas G1 is introduced from the upper portion side, the synthesis gas G1 is passed through the inside of the gas cooling tower 21 so as to form a descending current, and the synthesis gas G1 is cooled by water sprayed from the water spray openings 24 while passing through the inside of the gas cooling tower 21. In this case, the synthesis gas G1 is preferably discharged from the lower portion side of the gas cooling tower 21.

The temperature of the synthesis gas G1 that is introduced into the gas cooling tower 21 is sufficiently higher than 100° C., but the water that is sprayed from the water spray openings 24 is lower than 100° C. Therefore, the synthesis gas G1 is cooled due to the temperature difference and is also cooled by the vaporization heat generated when the water sprayed from the water spray openings 24 vaporizes. A part of the vaporized water is preferably mixed into the synthesis gas G1. A part or all of the water that is sprayed from the water spray openings 24 may be in a vaporized state when sprayed.

In the gas cooling tower 21, the synthesis gas G1 is preferably cooled to a temperature of 100° C. or higher and 200° C. or lower and preferably discharged to the outside of the gas cooling tower 21 within the above-described temperature range. When the synthesis gas G1 is cooled to 200° C. or lower, it is possible to purify the synthesis gas G1 in the filtration-type dust collector 22 to be described below without damaging the filtration-type dust collector 22 or degrading the dust collection performance. In addition, when the synthesis gas G1 is cooled to 100° C. or higher, the majority of the sprayed water is vaporized and mixed into the synthesis gas G1. Therefore, in the gas cooling tower 21, since a large amount of the sprayed water is not discharged, there is no need to introduce a large drain facility into the gas cooling tower 21.

Here, a part of water sprayed to the gas cooling tower 21 may drop downward in the gas cooling tower 21 as a liquid and be recovered. In addition, an impurity, such as char or tar, in the synthesis gas G1 may also collide with the sprayed water and be thereby dropped downward and recovered.

It is preferable that the synthesis gas G1 is cooled in the gas cooling tower 21 to a temperature of more preferably 120° C. or higher and 180° C. or lower and still more preferably 130° C. or higher and 170° C. or lower, cooled to these temperatures and discharged to the outside. When the synthesis gas G1 is cooled to 120° C. or higher, it is possible to prevent the water mixed into the synthesis gas G1 from liquefying in a large quantity in the gas cooling tower 21 and, furthermore, the filtration-type dust collector 22 to be described below. In addition, when the synthesis gas G1 is cooled to 180° C. or lower, it becomes easy to further avoid the damage or function degradation of the filtration-type dust collector 22.

(Filtration-Type Dust Collector)

The synthesis gas G1 cooled in the gas cooling tower 21 passes through the filtration-type dust collector 22. As the filtration-type dust collector 22, a dust collector called a so-called bag filter can be used, and the bag filter includes a casing and a filter medium accommodated in the casing. The filter medium is not particularly limited, and, for example, woven fabric such as a glass fiber and a PTFE fiber, felt or the like is used.

The synthesis gas G1 contains a large amount of a solid impurity such as tar or char, but the solid impurity is removed when the synthesis gas G1 passes through the filtration-type dust collector 22. When the solid impurity is removed, it is possible to prevent the sticking of the solid impurity in each device in the post-stage of the filtration-type dust collector 22. For example, in the organic substance generation portion 30, it is ordinary that gas is blown into a reactor through a sparger, and the sticking of the solid impurity in the sparger can be prevented. Furthermore, when the solid impurity is removed, it is easy to enhance the activity of the microbial catalyst in the organic substance generation portion 30, and it is possible to prevent the death of the microbial catalyst due to the influence of the impurity and to synthesize an organic substance at a high conversion efficiency.

In the present specification, "remove" means that the concentration of a target substance to be removed in the gas is reduced by removing at least a part of the target substance from the synthesis gas and is not limited to the complete removing of the target substance to be removed.

When the synthesis gas G1 is cooled in the gas cooling tower 21 as described above, the temperature of the synthesis gas G1 at the time of passing through the filtration-type dust collector 22 also becomes a temperature of preferably 100° C. or higher and 200° C. or lower, more preferably 120° C. or higher and 180° C. or lower and still more preferably 130° C. or higher and 170° C. or lower. Therefore, it is possible to prevent the high-temperature synthesis gas G1 from damaging the filtration-type dust collector 22 or degrading the filtration performance. In addition, it is also possible to prevent the synthesis gas G1 that is contained in the synthesis gas G1 from liquefying in a large quantity in the filtration-type dust collector 22.

(Water Scrubber)

In the present embodiment, the synthesis gas G1 discharged from the filtration-type dust collector 22 passes through the water scrubber 23 that is disposed in the post-stage of the filtration-type dust collector 22. The synthesis gas G1 contains a variety of impurities other than the above-described solid impurity, and, for example, a water-soluble impurity is contained. Examples of the water-soluble impurity include acidic gases such as hydrogen sulfide, hydrogen chloride and blue acid, basic gases such as ammonia and oxides such as NOx and SOx. These water-soluble impurities are removed when passing through the water scrubber 23.

In addition, the synthesis gas G1 also contains oil-based impurities such as BTEX (benzene, toluene, ethylbenzene and xylene), naphthalene, 1-naphthol and 2-naphthol, but these may also be removed appropriately in the water scrubber 23, and the solid impurity or the like that could not be recovered in the filtration-type dust collector 22 may also be appropriately removed.

The water scrubber 23 is not particularly limited as long as the water scrubber 23 is configured to bring the synthesis gas G1 and water into contact with each other and is, for example shown in FIG. 1, preferably configured to bring water sprayed from a nozzle 25 provided in the upper portion (for convenience, also referred to as "washing water") into contact with the synthesis gas G1. In this case, the water scrubber 23 is preferably provided with an introduction path 27, a supply path 28, a discharge path 29 and the like. In addition, a storage portion 26 that stores the washing water is provided in the lower portion of the water scrubber 23. The washing water stored in the storage portion 26 may be appropriately stirred with a stirring device, not shown.

The introduction path 27 is a path for introducing the synthesis gas G1 into the water scrubber 23, and an introduction opening 27A of the introduction path 27 is provided, for example, above the liquid surface of the washing water stored in the storage portion 26 in the water scrubber 23.

The supply path 28 supplies the washing water such that the water is circulated in the water scrubber 23 and brought into contact with the synthesis gas G1. Specifically, the supply path 28 makes the washing water stored in the storage portion 26 spray downward in the water scrubber 23 from the nozzle 25 to come into contact with the synthesis gas G1. Here, for example, a pump (not shown) is provided in the supply path 28, and the washing water is pneumatically sent to the nozzle 25 by the pump. In addition, the washing water is sprayed downward from the nozzle 25 in the water scrubber 23. The discharge path 29 is provided in the upper portion of the water scrubber 23 and discharges the synthesis gas G1 that has come into contact with the washing water sprayed from the nozzle 25 to the outside.

The washing water that is used in the water scrubber 23 may be water alone or a chemical may be added thereto as appropriate.

Furthermore, a removal device 19 may be provided in the water scrubber 23. The removal device 19 is a device for removing, for example, the impurities that are contained in the washing water (the oil-based impurities, the solid impurity, the water-soluble impurities and the like). The removal device 19 is preferably provided on a circulation path that circulates the water in the storage portion 26, for example. The removal device 19 preferably removes, for example, the oil-based impurities that are contained in the washing water, the solid impurity that does not dissolve in the washing water, the water-soluble impurities that dissolve in the washing water and the like. Therefore, the removal device 19 may be an oil-water separator or the like, may be a filter or the like that removes the solid impurity, may be a combination of two or more of these and may have any configuration as long as the impurities that are contained in the washing water can be removed. With providing the removal device 19, the water scrubber 23 prevents the accumulation of the impurities in the washing water.

The synthesis gas G1 is preferably cooled by coming into contact with water in the water scrubber 23. As described above, the synthesis gas G1 is cooled in the gas cooling tower 21 and introduced into the water scrubber 23 in a state of being cooled to a predetermined temperature (a temperature of preferably 100° C. or higher and 200° C. or lower, more preferably 120° C. or higher and 180° C. or lower and still more preferably 130° C. or higher and 170° C. or lower).

Incidentally, the temperature of the water that comes into contact with the synthesis gas G1 in the water scrubber 23 is lower than 100° C., preferably 0° C. or higher and 40° C. or lower and more preferably 5° C. or higher and 30° C. or lower.

As "the temperature of the water that comes into contact with the synthesis gas G1" in the present specification, in a case where the washing water is circulated and brought into contact with the synthesis gas G1 as described above, the temperature of the water immediately before coming into contact with the synthesis gas G1, that is, the water (washing water) sprayed from the nozzle 25 may be measured. In addition, in a case where the synthesis gas G1 is introduced into the stored water (washing water) as described below, the temperature of the washing water stored in the storage portion 26 may be measured.

The synthesis gas G1 comes into contact with the water having the above-described temperature in the water scrubber 23 and is thereby cooled to a temperature of, for example, lower than 100° C., preferably 40° C. or lower and more preferably 38° C. or lower. When the synthesis gas G1 is cooled to a predetermined temperature that is lower than the boiling point of water in the water scrubber 23 as described above, at least a part of water mixed into the synthesis gas G1 in the gas cooling tower 22 (water vapor) is condensed and removed. Therefore, it becomes possible to appropriately remove water even without separately providing a large device for removing the water mixed in the gas cooling tower 22. In addition, the synthesis gas G1 is cooled to 40° C. or lower, it is possible to supply the synthesis gas G1 having an appropriate temperature to the organic substance generation portion even without separately providing a cooling device. In addition, even in a case where a cooling device is included in a treatment device that is provided in the post-stage of the water scrubber 23, it is possible to reduce the load in the cooling device.

The synthesis gas G1 is preferably cooled to a temperature of, for example, 0° C. or higher by coming into contact with water and is preferably cooled to a temperature of 5° C. or higher.

It is preferable that the water scrubber 23 is provided with a temperature controller, not shown, and the temperature of the washing water is controlled with the temperature controller. The temperature controller may be attached to, for example, the supply path 28 to adjust the temperature of the washing water that passes through the inside of the supply path 28 or may be provided on the outer periphery of the water scrubber to adjust the temperature of the washing water stored in the storage portion 26 in the water scrubber. The temperature controller preferably puts the temperature of the washing water that passes through the supply path 28 or the washing water stored in the storage portion 26 into the above-described range by cooling or the like. In addition, the temperature of the water that is brought into contact with the synthesis gas G1 may be maintained within a certain temperature range by appropriately replacing the water that is stored in the storage portion 26.

In the above description, an aspect in which the synthesis gas G1 comes into contact with the washing water that is sprayed from the nozzle 25 in the water scrubber 23 has been described, but the synthesis gas G1 may be introduced into the washing water that is stored in the storage portion 26.

In this case, the supply path 28 and the nozzle 25 are not provided, and the washing water is not sprayed from the nozzle. In addition, the introduction opening 27A of the introduction path 27 is disposed below the liquid surface of the washing water stored in the storage portion 26. The synthesis gas G1 comes into contact with the washing water stored in the storage portion 26, whereby the synthesis gas G1 is washed and preferably cooled.

Even in a case where the synthesis gas G1 is introduced into the washing water that is stored in the storage portion 26, the temperature of the water that comes into contact with the synthesis gas G1 or the temperature of the synthesis gas G1 (that is, the temperature of the synthesis gas G1 that is introduced into the water scrubber 23 or the temperature of the cooled synthesis gas G1) is as described above.

(Other Treatment Devices)

The treatment unit 20 may have treatment device(s) other than the gas cooling tower 21, the filtration-type dust collector 22 and the water scrubber 23. Examples of such treatment device(s) include a heat exchanger that is provided in the pre-stage of the gas cooling tower 21. Therefore, the synthesis gas G1 discharged from the gasifier 11 may be supplied to the gas cooling tower 21 after passing through the heat exchanger. However, the synthesis gas G1 discharged from the gasifier 11 may be supplied to the gas cooling tower 21 without passing through the heat exchanger.

"The pre-stage" in the present specification means the pre-stage along the supply flow of the synthesis gas G1. In addition, "the post-stage" means the post-stage along the supply flow of gas of the synthesis gas G1. The supply flow of the synthesis gas G1 means the flow of the synthesis gas G1 while the synthesis gas G1 is discharged from the gasifier 11 and introduced into the organic substance generation portion 30.

The heat exchanger is a device that cools the synthesis gas G1 using a heat medium. The heat exchanger cools the synthesis gas G1 by transferring the heat energy of the synthesis gas G1 to the heat medium. As the heat exchanger, a boiler is preferably used. The boiler is a device in which water is communicated as a heat medium, the communicated water is heated by the heat energy of the synthesis gas G1 and turned into vapor. When the boiler is used as the heat exchanger, it becomes possible to easily heat other devices with vapor generated from the heat exchanger, and the heat energy of the synthesis gas G1 can be easily reused.

Here, the heat exchanger to be used can be a device other than the boiler and may have any configuration as long as the heat energy is transferred to the heat medium from the synthesis gas G1, but a partition type in which the synthesis gas G1 and the heat medium do not come into direct contact with each other is preferable. The heat medium may be any of gas or liquid and may be a heat medium accompanying a phase change between gas and liquid. In addition, the heat energy from the synthesis gas G1 may be transferred to the heat medium in a state of having passed through a path with a shape such as a tubular shape or a plate shape.

The temperature of the synthesis gas G1 discharged from the gasifier 11 becomes as high as, for example 900° C. or higher as described above. Therefore, when cooled with the heat exchanger, the synthesis gas G1 is supplied to the gas cooling tower 21 at a relatively low temperature, which makes it possible to prevent the synthesis gas G1 from being excessively cooled in the gas cooling tower 21. Therefore, it is possible to decrease the amount of water that is sprayed to the synthesis gas G1 in the gas cooling tower 21, and furthermore, it becomes unnecessary to supply the synthesis gas G1 having a high water content rate to the filtration-type dust collector 22 and the water scrubber 23. Therefore, it is possible to suppress the amount of water transferred to the water scrubber 23 from the gas cooling tower 21 and to prevent water from excessively agglomerating in the filtration-type dust collector 22.

As described above, the heat exchanger cools cools the synthesis gas supplied at a high temperature of, for example, 900° C. or higher to a temperature of, for example, 200° C. or higher and 300° C. or lower and preferably 240° C. or higher and 280° C. or lower and supplies the synthesis gas to the gas cooling tower 21. When the synthesis gas is cooled to 200° C. or higher, it is possible to pass the synthesis gas G1 through a heat exchanger 22 while preventing the precipitation of an impurity, and, when the synthesis gas is set to 240° C. or higher, since the precipitation of a tar component can be effectively prevented, clogging or the like in the heat exchanger 22 is less likely to occur. In addition, when the synthesis gas is set to 300° C. or lower, it becomes unnecessary to excessively cool the synthesis gas G1 in the gas cooling tower 21.

In addition, in the treatment unit 20, a treatment device (also referred to as "post-stage treatment device") may be provided in the post-stage of the water scrubber 23, and the synthesis gas G1 that has passed through the water scrubber 23 may be supplied to the organic substance generation portion 30 after being appropriately treated with the post-stage treatment device.

Examples of the post-stage treatment device include a moisture separator including a gas chiller or the like, a low-temperature separation type (deep cooling type) separator, a fine particle separator composed of a variety of filters, a desulfurization device (sulfide separator), a film separation type separator, a deoxidation device, a pressure swing adsorption type separator (PSA), a temperature swing adsorption type separator (TSA), a pressure/temperature swing adsorption type separator (PTSA), a separator in which activated carbon is used, a deoxidation catalyst, specifically, a separator in which a copper catalyst or a palladium catalyst is used, and the like. One of these may be used singly or two or more may be jointly used.

The synthesis gas G1 discharged from the water scrubber 23 may be further purified with the post-stage treatment device.

(Organic Substance Generation Portion)

As described above, the synthesis gas that has passed through at least the gas cooling tower 21, the filtration-type dust collector 22 and the water scrubber 23 is supplied to the organic substance generation portion 30 as the purified synthesis gas G2. In the organic substance generation portion 30, the purified synthesis gas G2 is brought into contact with the microbial catalyst to generate an organic substance. As the microbial catalyst, a gas-assimilating microbial is preferably used.

The organic substance generation portion 30 includes a fermenter (reactor) filled with a culture containing water and the microbial catalyst. The purified synthesis gas G2 is supplied to the inside of the fermenter, and the purified synthesis gas G2 is converted to an organic substance in the fermenter. The organic substance preferably contains ethanol.

As the fermenter, a continuous fermenting device is preferably used, and any of a stirring type, an air lift type, a cell tower type, a loop type, an open bond type and a photobio type may be used.

The purified synthesis gas G2 and the culture may be continuously supplied to the fermenter, but there is no need to supply the purified synthesis gas G2 and the culture at the same time, and the purified synthesis gas G2 may be supplied to the fermenter to which the culture has been supplied in advance. Ordinarily, the synthesis gas G2 is blown into the fermenter through a sparger or the like.

A culture medium that is used when the microbial catalyst is cultured is not particularly limited as long as the composition is appropriate depending on germs and is a liquid containing water, which is a main component, and nutrients (for example, vitamins, phosphoric acid and the like) dissolved or distributed in this water.

In the organic substance generation portion 30, an organic substance is generated due to the microbial fermentation of the microbial catalyst and an organic substance-containing liquid is obtained.

The temperature of the fermenter is preferably controlled to 40° C. or lower. When the temperature of the fermenter is controlled to 40° C. or lower, the microbial catalyst in the fermenter does not die, and the purified synthesis gas G2 comes into contact with the microbial catalyst, whereby an organic substance such as ethanol is efficiently generated.

The temperature of the fermenter is more preferably 38° C. or lower. In addition, in order to enhance the catalytic activity, the temperature is preferably 10° C. or higher, more preferably 20° C. or higher and still more preferably 30° C. or higher.

(Separator)

The device for producing an organic substance 10 includes a separator 31 that separates at least water from the organic substance-containing liquid. Examples of the separator 31 include a solid-liquid separator, a distillation device, a separation film and the like, and a solid-liquid separator and a distillation device are preferably used in combination. Hereinafter, a separation step that is carried out by combining a solid-liquid separator and a distillation device will be specifically described.

The organic substance-containing liquid obtained in the organic substance generation portion 30 is preferably separated into a solid component mainly containing a microbial and a liquid component containing the organic substance in the solid-liquid separator. The organic substance-containing liquid obtained in the organic substance generation portion 30 contains, in addition to the organic substance, which is a target substance, the microbial that was contained in the fermenter, the carcass thereof or the like and is thus separated into solid and liquid to remove these. As the solid-liquid separator, there are a filter, a centrifuge, devices in which a solution precipitation method is used and the like. In addition, the solid-liquid separator may be a device that separates the liquid component containing the organic substance from the solid component by evaporating the liquid component from the organic substance-containing liquid (for example, a heated-air dryer). At this case, the liquid component containing the organic substance, which is the target substance, may be fully evaporated or the liquid component may be partially evaporated such that the organic substance, which is the target, is preferentially evaporated.

The liquid component separated by the solid-liquid separator is distilled in the distillation device in order to further separate the organic substance, which is the target substance. The separation by distillation makes it possible to purify a large amount of the organic substance in high purity with simple operation.

In the case of carrying out the distillation, a well-known distillation device such as a distillation tower may be used. In addition, the distillation needs to be operated such that, for example, the organic substance, which is the target substance, (for example, ethanol) is contained in the distillate at a high purity and water is contained in the bottom product (that is, the distillation residue) as a main component (for example, 70 mass % or more and preferably 90 mass % or more). Such operation makes it possible to generally separate the organic substance, which is the target substance, and water.

The temperature in the distiller at the time of the distillation of the organic substance (for example, ethanol) is not particularly limited, but is preferably 100° C. or lower and more preferably approximately 70° C. to 95° C. When the temperature in the distillation device is set within the above-described range, it is possible to reliably separate the required organic substance and the other components such as water.

The pressure in the distillation device at the time of the distillation of the organic substance may be a normal pressure, but is preferably lower than the atmospheric pressure and more preferably approximately 60 to 150 kPa (gauge pressure). When the pressure in the distillation device is set within the above-described range, it is possible to improve the separation efficiency of the organic substance and to improve the yield of the organic substance.

The water separated in the separator 31 is preferably reused and more preferably supplied to the gas cooling tower 21 and used for water spray in the gas cooling tower 21. When the water is reused as described above, the water that became unnecessary in the organic substance generation portion 30 does not become drainage water, which is preferable from the viewpoint of the environmental protection and the viewpoint of the economic efficiency. In addition, in the device for producing an organic substance 10, the separator 31 and the gas cooling tower 21 may be connected to each other and a supply path 32 that supplies the water obtained in the separator 31 to the gas cooling tower 21 may be provided. The supply path 32 is not particularly limited, but is preferably made of a pipe or the like. In addition, the water separated in the separator 31 may be supplied to the gas cooling tower 21 after being further purified to have a higher purity.

As described above, according to the first embodiment, the synthesis gas G1 is cooled by water spray in the gas cooling tower 21, which makes it possible to cool the synthesis gas G1 without blowing nitrogen gas or an air. Therefore, it is possible to lower the temperature of the synthesis gas G1 without changing the composition of the synthesis gas G1, and it is possible to synthesize the organic substance without causing the death of the microbial catalyst. In addition, since the synthesis gas G1 is passed through the filtration-type dust collector 22 after the temperature of the synthesis gas G1 is lowered, it is possible to purify the synthesis gas G1 without causing the breakage, performance degradation or the like of the filtration-type dust collector 22. In addition, water cooling is used, whereby it is possible to cool the synthesis gas G1 without using a large amount of energy.

Therefore, it is possible to synthesize an organic substance at a high conversion efficiency while the energy or the like is used to the minimum extent and clogging or the like in each device in the post-stage is not caused.

In addition, the synthesis gas G1 that has passed through the filtration-type dust collector 22 is passed through the water scrubber 23, whereby it is possible to remove the water mixed into the synthesis gas G1 in the gas cooling tower 21 while the synthesis gas G1 is washed and cooled in the water scrubber 23. When the water scrubber 23 is provided in the post-stage of the filtration-type dust collector 22 as described above, since the water scrubber 23 exhibits a variety of functions, it is possible to synthesize an organic substance at a high conversion efficiency while the device is simplified.

In the first embodiment, a configuration in which the water scrubber is provided has been described, but the water scrubber may not be provided. In a case where the water scrubber is not provided, the synthesis gas G1 that has passed through at least the gas cooling tower 21 and the filtration-type dust collector 22 is brought into contact with the microbial catalyst and converted to an organic substance in the organic substance generation portion 30. The synthesis gas G1 that is discharged from the filtration-type dust collector 22 in the present embodiment typically has a relatively high temperature (for example, 100° C. or higher), and, in a case where the water scrubber is not provided, a cooling device other than the water scrubber may be provided in the post-stage of the filtration-type dust collector 22, and the synthesis gas G1 discharged from the filtration-type dust collector 22 may be cooled with the cooling device other than the water scrubber.

In addition, in a case where the water scrubber is not provided, not only the cooling device but also one or more treatment devices selected from the above-described post-stage treatment devices may be provided in the post-stage of the filtration-type dust collector, and the synthesis gas G1 discharged from the filtration-type dust collector may be treated as appropriate with the post-stage treatment devices.

In addition, in a case where there is no need to purify the organic substance produced in the organic substance generation portion 30, a case where there is no need to separate water from the organic substance-containing liquid or the like, the separator 31 may not be provided.

In the present embodiment, the purified synthesis gas G2 is also produced with the gasifier 11 and the treatment unit 20. Therefore, the present embodiment also provides a device for producing a purified synthesis gas including the gasifier 11 and the treatment unit 20 and a method for producing a purified synthesis gas.

The treatment unit 20 in the device for producing a purified synthesis gas includes at least the gas cooling tower 21 and the filtration-type dust collector 22 as described above and preferably further includes the water scrubber 23. In addition, the treatment unit 20 may additionally have a post-stage treatment device, a heat exchanger or the like as appropriate. These have been described above in detail and thus will not be described again.

In addition, in the first embodiment described above, an aspect in which the organic substance generation portion 30 is provided and an organic substance is produced has been described, but the organic substance generation portion 30 may not be provided. In an aspect in which the organic substance generation portion 30 is not provided, the purified synthesis gas G2 generated with the gasifier 11 and the treatment unit 20 may be used in, for example, uses other than the generation of an organic substance or may be transported to a different place and used in a use in which the purified synthesis gas G2 is converted to an organic substance.

Furthermore, in the first embodiment, an aspect in which the synthesis gas G1 is obtained from waste in the gasifier 11 has been described, but the synthesis gas G1 may be generated from a substance other than waste in the gasifier 11. For example, the synthesis gas G1 may be generated from fossil resources such as natural gas, coal, heavy oil, petroleum discharged gas and oil shale, biomass other than waste or the like. In addition, the synthesis gas G1 may be a gaseous by-product in a variety of production processes such as a steel production process, and, for example, the gasifier 11 may configure a steel production facility or the like.

REFERENCE SIGNS LIST

10 Device for producing organic substance
11 Gasifier
12 Gasification furnace
13 Reforming furnace
21 Gas cooling tower
22 Filtration-type dust collector
23 Water scrubber
24 Water spray opening
25 Nozzle
26 Storage portion
27 Introduction path
28 Supply path
29 Discharge path
30 Organic substance generation portion
31 Separator
G1 Synthesis gas
G2 Purified synthesis gas

The invention claimed is:

1. A method for producing an organic substance comprising:
a step of passing a synthesis gas discharged from a gasifier through a gas cooling tower to cool the synthesis gas with water sprayed in the gas cooling tower;
a step of passing the synthesis gas cooled in the gas cooling tower through a filtration-type dust collector, and
a step of bringing the synthesis gas that has passed through at least the gas cooling tower and the filtration-type dust collector into contact with a microbial catalyst to generate an organic substance,
wherein the synthesis gas contains:
0.1 vol % or more and 80 vol % or less of carbon monoxide,
0.1 vol % or more and 80 vol % or less of hydrogen, and
0.01 vol % or more and 5 vol % or less of oxygen, and
wherein oxygen is removed from the synthesis gas by a deoxidation device and carbon dioxide is removed from the synthesis gas by at least one selected from the group consisting of a pressure swing adsorption type separator, a temperature swing adsorption type separator, and a pressure/temperature swing adsorption type separator.

2. The method for producing an organic substance according to claim 1,
wherein a temperature of the synthesis gas discharged from the gasifier is 900° C. or higher.

3. The method for producing an organic substance according to claim 1,
wherein the synthesis gas is cooled to a temperature of 100° C. or higher and 200° C. or lower in the gas cooling tower.

4. The method for producing an organic substance according to claim 1,
wherein the synthesis gas discharged from the filtration-type dust collector is further passed through a water scrubber, and
the synthesis gas that has passed through at least the gas cooling tower, the filtration-type dust collector and the water scrubber is brought into contact with a microbial catalyst to generate an organic substance.

5. The method for producing an organic substance according to claim 4,
wherein the synthesis gas is cooled to 40° C. or lower in the water scrubber.

6. The method for producing an organic substance according to claim 4,
wherein the water sprayed in the gas cooling tower is vaporized and mixed into the synthesis gas, and
at least a part of water mixed into the synthesis gas is condensed and removed in the water scrubber.

7. The method for producing an organic substance according to claim 1,
wherein the organic substance is generated in a reactor filled with at least the microbial catalyst and water,
water is separated from an organic substance-containing liquid containing the organic substance obtained in the reactor, and the separated water is supplied to the gas cooling tower.

8. The method for producing an organic substance according to claim 1,
wherein the gasifier gasifies waste to generate a synthesis gas.

9. The method for producing an organic substance according to claim 1,
wherein the organic substance contains ethanol,
a filtration-type dust collector through which the synthesis gas cooled in the gas cooling tower is passed.

* * * * *